United States Patent [19]
Christensen et al.

[11] 4,219,462
[45] Aug. 26, 1980

[54] 6-METHYL PENICILLINS

[75] Inventors: Burton G. Christensen, Scotch Plains; Lovji D. Cama, Edison, both of N.J.

[73] Assignee: Merck & Co., Inc., Rahway, N.J.

[21] Appl. No.: 492,812

[22] Filed: Jul. 29, 1974

Related U.S. Application Data

[63] Continuation-in-part of Ser. No. 194,018, Oct. 29, 1971, abandoned, which is a continuation-in-part of Ser. No. 149,349, Jun. 2, 1971, abandoned.

[51] Int. Cl.² ........................................... C07D 499/42
[52] U.S. Cl. ............................. 260/245.2 R; 424/270; 424/271
[58] Field of Search .......................... 260/239.1, 245.2

[56] References Cited
U.S. PATENT DOCUMENTS 4,071,529  1/1978  Christensen et al. ............. 260/245.2

Primary Examiner—Nicholas S. Rizzo
Attorney, Agent, or Firm—Frank M. Mahon; Hesna J. Pfeiffer; Rudolph J. Anderson

[57] ABSTRACT

New 6-methyl penicillins and the corresponding 6-aminopenicillanic acid compounds and processes for the preparation of these penicillins are provided. The new penicillins are antibiotics which are active against various gram-negative and gram-positive pathogens.

1 Claim, No Drawings

6-METHYL PENICILLINS

CROSS-REFERENCE TO RELATED APPLICATIONS

This is a continuation-in-part of our copending application Ser. No. 194,018, filed Oct. 29, 1971, now abandoned, which was in turn a continuation-in-part of our copending application Ser. No. 149,349, filed June 2, 1971, now abandoned. This case is also a continuation-in-part application of copending Ser. No. 149,349.

BACKGROUND OF THE INVENTION

The discovery of penicillin and the subsequent development of various semi-synthetic penicillins provided doctors with a valuable armamentarium for the treatment of infections due to various pathogenic microorganisms. However, these antibiotics, as well as other new antibiotics, have several deficiencies. Thus, in general, they are active against only a particular group of organisms and, more importantly, their use has resulted in the emergence of resistant strains of pathogens against which the known antibiotics are inactive. The search, therefore, has continued to find new antibiotics to overcome the deficiencies of the known products. In particular, modifications of the penicillin molecule have been sought in an effort to provide new and more active antibiotics. For example, it had been postulated that the introduction of a methyl group in place of the hydrogen α to the lactam would provide products of enhanced activity and many chemists in this field tried unsuccessfully to produce such penicillins.

SUMMARY OF THE INVENTION

This invention is concerned with new penicillins having a methyl substituent in place of hydrogen on the carbon α to the lactam. These new penicillins can be represented by the following formula:

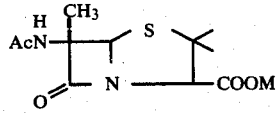

in which Ac represents an acyl group, and M represents hydrogen, a metal cation, an amine or a pharmaceutically acceptable ester group or an easily removable ester group.

These new penicillins are useful in the control and treatment of gram-negative and gram-positive bacterial infections. These 6-substituted penicillins have activity against gram-negative organisms. They are active against many bacteria, including in vivo against *Proteus morganii*, and in addition, effective against the following gram-negative bacteria: *Escherichia coli, Proteus vulgaris, Proteus mirabilis, Salmonella schottmuelleri, Klebsiella pneumoniae AD, Klebsiella pneumoniae B,* and *Paracolobactrum arizoniae*. Specific bacterial activity is dependent upon the exact structure of the final product; not all compounds being active against all organisms.

The new penicillins of this invention are prepared by the acylation of the corresponding substituted 6-aminopenicillanic acid compounds. This embodiment of the present invention can be illustrated by the following reactions:

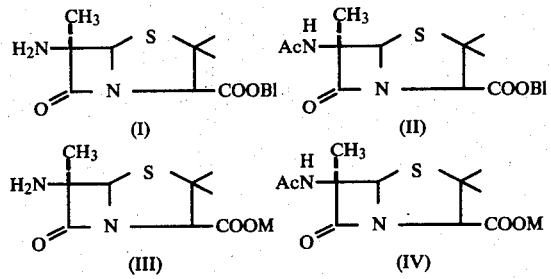

wherein Bl represents a blocking group, Ac represents an acyl group and M represents hydrogen, a metal cation, an amine, or an ester. Thus, in accordance with the foregoing flowsheet, the 6α-methyl-6β-aminopenicillinate (I) is acylated to form the corresponding penicillin derivative (II) which is deblocked to form the desired penicillin (IV) or a salt or ester thereof. Alternatively, the starting material can first be deblocked to produce the corresponding acid or a salt thereof (III) and this intermediate can then be acylated to obtain the desired penicillin or a salt thereof.

DESCRIPTION OF THE PREFERRED EMBODIMENT

In accordance with specific embodiments of this invention, the new 6-methyl penicillins of the formula

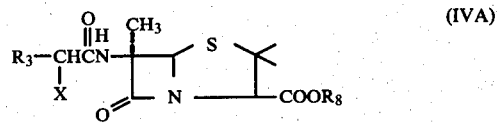

are produced by the acylation of the corresponding 6-methyl-6-aminopenicillanic acid compound of the formula

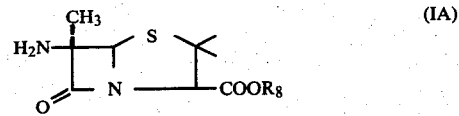

In the above formulas, $R_8$ represents a blocking group such as benzyl, trichloroethyl, trimethylsilyl, phenacyl, or methoxymethyl, hydrogen, or salts thereof when $R_8$ is hydrogen. The acyl group of formula IVA above is represented by the substituent

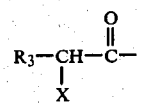

wherein X is hydrogen, halogen, amino, guanidino, phosphono, hydroxy, tetrazolyl, carboxy, sulfo, or sulfamino and $R_3$ is phenyl, substituted phenyl, a monocyclic heterocyclic 5- or 6-membered ring containing one or more oxygen, sulfur or nitrogen atoms in the ring, substituted heterocycles, phenylthio, phenyloxy, heterocyclic or substituted heterocyclic thio groups, loweralkyl (1-6 carbon atoms), or cyano; the substituents on the $R_3$ group being halo, carboxymethyl, guanidino, guanidinomethyl, carboxamidomethyl, aminomethyl, nitro, methoxy or methyl.

Preferably, in the compound of formula IVA above, X is hydrogen, amino, or carboxyl and $R_3$ is phenyl, phenoxy, loweralkyl or a 5- or 6-membered heterocyclic ring having one or two sulfur, oxygen or nitrogen hetero atoms.

The acylation of the 6-methyl-6-aminopenicillanic acid compound is readily effected by reaction with an acylating agent such as an acyl halide (chloride or bromide) or a functional equivalent thereof such as an acid anhydride, a mixed acid anhydride with other carboxylic acids and particularly lower aliphatic esters of carboxylic acid, a carboxylic acid in the presence of a carbodiimide such as 1,3-dicyclohexylcarbodiimide, an activated ester of the carboxylic acid such as the p-nitrophenyl ester and the like, or enzymatic acylation pursuant to acylation methods used for the preparation of penicillins which are well known in this art.

As discussed above, the 6-methyl-6-aminopenicillanic acid compound acylated can be a suitably blocked ester, such as the benzyl, trichloroethyl, trimethylsilyl, phenacyl or methoxymethyl ester which is removed in accordance with procedures known in the art to produce the desired penicillin or a salt thereof. Thus, for example, the blocking group can be benzyl which is readily removed by hydrogenolysis at room temperature in a suitable solvent medium, for example, aqueous methanol in the presence of a noble metal catalyst, preferably palladium on carbon. Alternatively, the 6-methyl-6-aminopenicillanic acid ester can be first converted to the free acid and the salt of the free acid, such as the sodium salt or an amine salt, can be acylated pursuant to procedures well known in the art which are used for the conversion of 6-aminopenicillanic acid to produce various penicillins.

The following examples illustrate processes for carrying out the present invention.

EXAMPLE 1

Sodium 6α-aminomethyl-6β-phenoxyacetamidopenicillanate

A. Benzyl 6α-azidomethyl-6β-phenoxyacetamidopenicillanate

A mixture of 132 mg. of p-toluenesulfonic acid monohydrate and 137 mg. of finely ground 2,4-dinitrophenylhydrazine is stirred for 0.5 hour in 3 ml. of absolute ethanol. To the slurry is added 340 mg. of benzyl 6α-azidomethyl-6β-(4-nitrobenzylideneamino)penicillanate in 3 ml. of absolute ethanol and 2 ml. of methylene chloride, washed in with another 3 ml. of ethanol, and the mixture is stirred for 0.8 hours. Filtration and evaporation of the filtrate at or below room temperature under reduced pressure gives, after washing the residue with ether, benzyl 6α-azidomethyl-6β-aminopenicillanate tosylate salt as a crystalline yellow solid. To this is added, with stirring in an ice bath, 132 mg. of phenoxyacetyl chloride in 3 ml. of methylene chloride and 335 mg. of $K_2HPO_4$ in 3 ml. of water, rinsed in with another 2 ml. each of water and methylene chloride. After vigorously stirring for 20 minutes at 0° C., the mixture is treated with 62 µl of pyridine, stirred for 5 more minutes, and allowed to settle. The phases are separated and the aqueous phase further extracted with 2 ml. of methylene chloride and 2 ml. of ether. The organic phases are combined, dried with magnesium sulfate, and concentrated to a gum under reduced pressure. The 347 mg. of crude product so obtained are purified by preparative tlx on four 1000µ 8"×8" silica plates developed with 5% ethyl acetate in chloroform. By this procedure, 282 mg. of benzyl 6α-azidomethyl-6β-phenoxyacetamidopenicillanate is obtained: ir ($CHCl_3$) NH (2.9–3.1 µ), azide (4.74 µ), β-lactam (5.60 µ), ester (5.72 µ), and amide (5.92 µ). The nmr spectrum ($CDCl_3$) exhibits peaks at 444–403 (complex 11H; main peaks at 436 and 415), 327 (1H), 308 (2H), 269 (2H), 266 (1H), 241 (2H), 84 (3H), and 81 (3H).

B. Sodium 6α-aminomethyl-6β-phenoxyacetamidopenicillanate

Hydrogenolysis of benzyl 6α-azidomethyl-6β-phenoxyacetamidopenicillanate in the presence of palladium on charcoal as described in Example 1 leads to concomitant reduction of the azidomethyl function to an aminomethyl function. The product obtained has an nmr ($D_2O$) spectrum with peaks at 448–407 (complex 10H; main peak at 420), 332 (1H), 283 (2H), 279 (strong $H_2O$ peak), 254 (1H), 224 (2H), 92 (3H), and 86 (3H) expressed in cps downfield from tms. Some pH dependence is noted in the positions of the 254 and 224 cps peaks.

The benzyl 6α-azidomethyl-6β-(4-nitrobenzylideneamino)penicillanate used as the starting material in A above is prepared as follows: A mixture of 2.94 g. of benzyl 6β-(4-nitrobenzylideneamino)-6α-hydroxymethylpenicillanate and 1.57 g. of p-nitrobenzenesulfonyl chloride in 20 ml. of dry methylene chloride is stirred and treated with 915 mg. of diisopropyl ethyl amine in 5 ml. of dry methylene chloride. Stirring is continued for 4.5 hours, after which the solution is washed with water, 1.24 g. $K_2HPO_4$ in water, and water again, dried with magnesium sulfate and concentrated to a foam: 4.1 g. Chromatography on 120 g. silica gel packed in benzene. After 1.7–1.8 liters of benzene eluate have been removed, tlc indicates the emergence of the desired material which is obtained in the next 300–400 ml. giving ca 1.3 g. of benzyl 6α-(4-nitrobenzenesulfonyloxymethyl)-6β-(4-nitrobenzylideneamino)penicillanate. The ir ($CHCl_3$) shows essentially no OH, and bands for β-lactam (5.62 µ) and ester (5.71 µ). The nmr ($CDCl_3$) shows peaks at 518 (1H), 500–465 (complex pair of quartets, 8H), 442 (5H), 327 (1H), 312 (2H), 277 (2H), 260 (1H), 89 (3H), and 82 (3H), expressed in cps downfield from tms.

A mixture of 575 mg. of lithium chloride and 883 mg. of sodium azide is stirred overnight with 13.6 ml. of sieve dried DMSO. The suspension is filtered and 500 mg. of benzyl 6α-(4-nitrobenzenesulfonyloxymethyl)-6β-(4-nitrobenzylideneamino)penicillanate is dissolved in 8.2 ml. of the supernatant liquid. After standing at room temperature for 2.8 hours, the mixture is poured into 30 ml. of ice water and 30 ml. of ethyl acetate. After shaking and phase separation, the aqueous layer is again extracted with ethyl acetate, the combined organic layers are dried with magnesium sulfate and the solution concentrated to 397 mg. of oil. After purification by preparative tlc on five 1000µ 8"×8" silica plates developed with 5% ethyl acetate in chloroform, 340 mg. of product are obtained. The ir ($CHCl_3$) shows azide (4.76 µ), β-lactam (5.66 µ) and ester (5.71 µ) bands; the nmr ($CDCl_3$) exhibits peaks at 517 (1H), 492, 483, 472, 464 (4H), 435 (5H), 325 (1H), 308 (2H), 261 (1H), 229 (2H), 89 (3H), and 83 (3H), expressed in cps downfield from tms.

The starting benzyl 6β-(4-nitrobenzylideneamino)-6α-hydroxymethylpenicillanate is prepared by purifying the crude product as follows: crude benzyl 6β-4- nitrobenzylideneamino-6α-hydroxymethylpenicillanate is purified by preparative tlc on silica gel with fluorescent indicator using 20% ethyl acetate in benzene. The yellow band which shows a dark band under either long or short wave length uv light, and which is usually preceded by a deep yellow (visible light) band, is removed and eluted with ethyl acetate to afford benzyl 6β-(4-nitrobenzylideneamino)-6α-hydroxymethylpenicillanate. The ir (CHCl₃) shows OH (2.8–3.1 μ), β-lactam (5.65 μ) and ester (5.72 μ) to be present and the nmr shows the benzylidene and C₅-protons as sharp singlets at 532 and 338 ppm downfield from tms in CDCl₃.

EXAMPLE 2

Sodium 6α-methyl-6β-phenoxyacetamidopenicillanate

A. Benzyl 6α-iodomethyl-6β-phenoxyacetamidopenicillanate

By the procedure corresponding to that described in Example 1A above, benzyl 6α-iodomethyl-6β-(4-nitrobenzylideneamino)penicillanate is converted to benzyl 6α-iodomethyl-6β-phenoxyacetamidopenicillanate. The nmr spectrum (CDCl₃) shows peaks at 443–401 (complex of 11H; main peaks at 435 and 414), 322 (1H), 307 (2H), 268 (2H), 265 (1H), 258, 248, 229, 218 (2H), and 82 (6H).

Sodium 6α-methyl-6β-phenoxyacetamidopenicillanate

Reduction of benzyl 6α-iodomethyl-6β-phenoxyacetamidopenicillanate with hydrogen in the presence of palladium on charcoal leads to concomitant reduction of the iodomethyl function to a methyl group; hence, two equivalents of sodium bicarbonate are used to neutralize the acids generated. Removal of sodium iodide from the lyophilizate is accomplished by generating the free penicillanic acid in concentrated aqueous solution at 0° C. with dilute phosphoric acid and rapidly extracting with cold ethyl acetate. The free acid (in CDCl₃) exhibits an nmr spectrum with peaks at 448–404 (complex 10–11H with main peak at 419), 325 (1H), 272 (2H), 265 (1H), 109 (3H), and 90 (6H), expressed in cps downfield from tms. Treatment with one equivalent of sodium bicarbonate solution and lyophilization gives the sodium salt which exhibits an nmr spectrum (D₂O) with peaks at 450–408 (complex 10H; main peak at 421) 321 (1H), 278 (intense water peak, obscuring φOCH₂CO), 251 (1H), 104 (3H), and 86 (6H) expressed in cps downfield from tms.

The benzyl 6α-iodomethyl-6β-(4-nitrobenzylideneamino)penicillanate used as the starting material in A above as prepared as follows: A solution of 591 mg. of lithium iodide (Fluka) in 4.3 ml. of sieve dried DMSO is prepared and to it is added 300 mg. of benzyl 6α-(4-nitrobenzenesulfonyloxy-methyl)-6β-(4-nitrobenzylideneamino)penicillanate. The solution is stirred for 48 hours at room temperature and worked up and purified in the azidomethyl series to give 189 mg. of benzyl 6α-iodomethyl-6β-(4-nitrobenzylideneamino)penicillanate as a yellow foam. The ir spectrum (CHCl₃) shows β-lactam (5.64 μ) and ester (5.71 μ) peaks, while the nmr (CDCl₃) shows peaks at 523 (1H), 502, 493, 473, 474 (4H), 444 (5H), 329 (1H), 314 (2H), 264 (1H), 226 (2H), 91 (3H), and 85 (3H), expressed in cps downfield from tms.

EXAMPLE 3

Sodium 6α-methyl-6β-(2-phenylacetamido)penicillanate

A. Benzyl 6α-methyl-6β-(2-phenylacetamido)penicillanate

Benzyl 6α-methyl-6β-aminopenicillanate (3 g.) is dissolved in 80 ml. CH₂Cl₂ and treated with 3 ml. pyridine, followed by 1.16 g. phenylacetyl chloride in 20 ml. CH₂Cl₂, which is stirred in over 3 minutes. After another 3 minutes, the solvent is evaporated and replaced with 100 ml. benzene, which is washed successively with water, water with pH 2 phosphate buffer, water, and water with pH 8 phosphate buffer. After drying with MgSO₄, filtration and evaporation, 3 g. of crude product is obtained. Chromatography on 120 g. silica gel and elution with chloroform affords crystalline benzyl 6α-methyl-6β-(2-phenylacetamido)penicillanate (1.0 g.) which is recrystallized from benzene-cyclohexane. m.p. 143°–145° C. nmr: 1.25, 1.3δ (gem. dimethyl), 1.7δ (6α-methyl), 3.5δ (φCH₂C=O), 4.3δ (3-H), 5.1δ (OCH₂φ), 5.3δ (5α-H), 6.0δ (NH), 7.1, 7.2δ (2 φ's). ir: NH 2.9 μ, β-lactam 5.61 μ, ester 5.71 μ, amide 5.95 μ. ms: 438, 250, 248, 189, 174.

B. Sodium 6α-methyl-6β-(2-phenylacetamido)penicillanate

Benzyl 6α-methyl-6β-(2-phenylacetamido)penicillanate (500 mg.) is hydrogenated at 40 psi for one hour in 50 ml. methanol and 12 ml. water with 500 mg. of 10% Pd/C and 96 mg. NaHCO₃. The mixture is filtered and lyophilized, affording 404 mg. of the title compound. nmr: (in D₂O with HOD at 4.4δ) 1.18, 1.20δ (gem. dimethyl), 1.45δ (6α-methyl), 3.3δ (φCH₂C=O), 3.9δ (3-H), 5.0δ (5α-H), 7.0δ (φ). ir: 5.67 μ (β-lactam), 5.98 μ (amide), 6.2–6.3 μ (COONa).

The benzyl 6α-methyl-6β-aminopenicillanate used as the starting material in A above is prepared as follows: Benzyl 6-(p-nitrobenzylideneamino)penicillanate (110 mg.) is dissolved in 4 ml. dry tetrahydrofuran. At −78° C. under a nitrogen atmosphere 0.109 ml. 2.3 M phenyllithium is added, forming benzyl 6α-lithio-6β-(p-nitrobenzylideneamino)penicillanate.

To this compound is added at −78° C. under nitrogen a solution of 0.2 ml. methyl iodide in 5 ml. of dry dimethylformamide. The mixture is stirred 5 minutes at −78° C. and then allowed to warm to room temperature over about 20–30 minutes. Benzene (50 ml.) is added, and the solution is washed six times with water; the second wash is acidified with pH 2 and the fifth with pH 8 phosphate buffers. The solution is dried with magnesium sulfate, filtered and evaporated in vacuo, affording 130 mg. of benzyl 6α-methyl-6β-(p-nitrobenzylideneamino)penicillanate. nmr: 1.4, 1.5δ (gem. dimethyl), 1.8δ (6α-methyl), 4.3δ (3-H), 5.2δ (OCH₂φ), 5.3δ (5α-H), 8.8δ (—CH=N), 9 aromatic H at 7.3–8.5. ir: β-lactam and ester carbonyls at 5.64 and 5.71 μ, respectively.

The latter compound (130 mg.) is treated with 50 mg. 2,4-dinitrophenylhydrazine and 48 mg. p-toluenesulfonic acid hydrate in 5 ml. ethanol 2BA for one-half hour. The mixture is filtered and the precipitate washed several times with ethanol. The filtrate is evaporated and the residue washed quickly with a little ether. The residue is then treated with aqueous K₂HPO₄ and extracted twice with ether. After drying the ether with MgSO₄, filtering and evaporating, 75 mg. crude product is obtained. Preparative layer chromatography on silica gel, eluting with 4:1 chloroform-ethyl acetate, affords pure benzyl 6α-methyl-6β-aminopenicillanate (19.5 mg.). nmr: 1.42, 1.59δ (gem. dimethyl), 1.59δ (6α-methyl), 1.85δ (NH$_2$), 4.44δ (3-H), 5.20δ (OCH$_2\phi$), 5.24δ (5α-H), 7.38δ (aromatic H). ir: β-lactam and ester carbonyls at 5.61 and 5.71 μ, respectively. ms: Strong 320, 292, 250, 130.

EXAMPLE 14

Sodium 6-phenylacetamido-6-methylpenicillanate

A. Ethyl α-azido-α-formylpropionate

To a solution of ethyl α-bromo-α-formylpropionate (20 g.) in dimethoxyethane (200 ml.) is added a solution of sodium azide (8 g.) in water (40 ml.) and the mixture is stirred at room temperature for 5 hours. The dimethoxy ethane is removed under reduced pressure and the residue is taken up in a mixture of ether and water. The ethereal phase is separated, washed with water, dried over anhydrous sodium sulfate and evaporated yielding ethyl α-azido-α-formylpropionate which is purified by vacuum distillation.

B. Ethyl α-azido-α-methyl-4-benzyloxycarbonyl-5,5-dimethyl-2-thiazolidine acetate To a solution of ethyl α-azido-α-formylpropionate (25.6 g.) in 95% ethanol (200 ml.) is added a solution of penicillamide hydrochloride (27.9 g.) and sodium acetate (18.5 g.) in water (200 ml.). The mixture is stored at room temperature for 24 hours then cooled to 0° C. and the product precipitated by the slow addition of water (400 ml.). The supernatant solution is decanted and the precipitate is taken up in methylene chloride, washed with water and dried over anhydrous sodium sulfate. To the methylene chloride solution containing ethyl α-methyl-α-azido-4-carboxy-5,5-dimethyl-2-thiazolidine acetate is added an ethereal solution of phenyldiazomethane in portions until the pink color of the reagent persists for 30 minutes. A few drops of acetic acid are added to decolorize the diazo compound and the solution is washed with aqueous sodium bicarbonate, dried over anhydrous sodium sulfate and evaporated leaving ethyl α-azido-α-methyl-4-benzyloxycarbonyl-5,5-dimethyl-2-thiazolidine acetate as a viscous yellow oil.

C. α-Methyl-α-azido-4-benzyloxycarbonyl-5,5-dimethyl-2-thiazolidineacetic acid To a solution of ethyl α-azido-α-methyl-4-benzyloxycarbonyl-5,5-dimethyl-2-thiazolidine acetate (3.92 g.) in ethanol (20 ml.) is slowly added 20 ml. of 0.5 N sodium hydroxide solution. The solution is stirred at room temperature overnight, then acidified with 20 ml. of 0.5 N hydrochloric acid. The product is extracted into ethyl acetate and the solution dried over anhydrous sodium sulfate and evaporated leaving α-methyl-α-azido-4-benzyloxycarbonyl-5,5-dimethyl-2-thiazolidineacetic acid.

D. Benzyl 6β-azido-6α-methylpenicillanate

To a cold solution of α-methyl-α-azido-4-benzyloxycarbonyl-5,5-dimethyl-2-thiazolidineacetic acid (1.82 g.) in dioxane (20 ml.) is added dicyclohexylcarbodiimide (1.1 g.). The solution is stirred for 30 minutes in an ice bath and then for two hours at room temperature. The precipitated dicyclohexylurea is removed by filtration and the filtrate is evaporated under reduced pressure. The residue is chromatographed on 40 g. of silica gel. Elution with benzene-hexane mixtures yields benzyl 6β-azido-6α-methylpenicillanate.

E. 6β-amino-6α-methylpenicillanic acid

A solution of benzyl 6β-azido-6α-methylpenicillanate (1.5 g.) in dioxane (100 ml.) and water (50 ml.) is hydrogenated in the presence of 10% Pd/C catalyst (1.5 g.) at 40 psi for three hours at room temperature. The catalyst is removed by filtration and the filtrate is lyophilized giving 6β-amino-6α-methylpenicillanic acid.

F. Sodium 6β-phenylacetamido-6α-methylpenicillanate

To a solution of 6β-amino-6α-methylpenicillanic acid (0.46 g.) in 4% potassium bicarbonate (14 ml.) and acetone (8 ml.) is added dropwise with stirring and ice cooling a solution of phenylacetyl chloride (0.35 ml.) in acetone (6 ml.) over a period of 10 minutes. After an additional 30 minutes, the acetone is removed under reduced pressure and the aqueous phase is extracted with ether. The aqueous phase is overlayered with ethyl acetate and acidified with 10% phosphoric acid to pH 2.5. The ethyl acetate phase is separated, washed once with cold water and vigorously stirred with water as the pH is adjusted to 6.5 with sodium bicarbonate. The aqueous phase is separated and lyophilized leaving sodium 6β-phenylacetamido-6α-methylpenicillanate as a white powder.

The new 6-methyl penicillins of the present invention are active against various gram-negative and gram-positive organisms and are therefore useful as bactericides. For this purpose, the new penicillins are preferably used in the form of their metal salts, particularly alkali metal salts such as sodium or potassium, or in the form of a salt of an amine such as trialkylamines, including triethylamine, procaine, dibenzylamine, N-benzyl-β-phenethylamine, 1-ephenamine, N,N'-dibenzylethylenediamine, dehydroabietylamine, N,N'-bis-dehydroabietylethylenediamine, N-(lower)alkylpiperidines, e.g., N-ethylpiperidine, and other amines which have been used to form salts with benzylpenicillin.

Aqueous solutions of the new penicillins or a salt thereof can be used as a bactericide for the removal of susceptible organisms from medical and dental equipment and the like. For this purpose they can be used in the form of a 1–5% aqueous solution. They can also be used for the isolation of microorganisms from mixtures of microorganisms. Further, they are useful as growth promoting agents for poultry. For example, the new penicillins can be added in small amounts to chick feeds in the form of a suitable salt such as the sodium, potassium or benzyl ammonium salt.

The new penicillins of this invention can be used alone or in combination as the active ingredient in any one of a variety of pharmaceutical preparations for animal or human therapy. These new antibiotics in the form of a non-toxic metal salt such as the sodium, potassium, calcium, aluminum or a non-toxic amine salt can be employed in capsule form or as tablets, powders, liquid solutions, suspensions or elixirs which can be prepared in the same manner as with the known penicillins for oral, intravenous or intramuscular administration. Suitable non-toxic carriers for such preparations that might be mentioned are mannitol, sucrose, glucose, sterile liquids such as water, saline and the like, glycols, and petroleum, animal and vegetable oils. Also, in addition to the carrier such pharmaceutical forms can include other ingredients such as stabilizers, binders, antioxidants, preservatives, lubricators, suspending agents, viscosity agents or flavoring agents and the like. In addition, there may be included other active ingredients including other antibiotics to provide a broader spectrum of antibiotic activity.

We claim:

1. A compound of the formula:

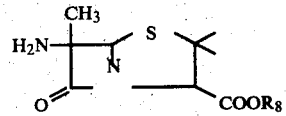

wherein: $R_8$ is hydrogen, benzyl, trichloroethyl, trimethylsilyl or a pharmaceutically acceptable cation thereof when $R_8$ is hydrogen.

* * * * *